(12) United States Patent
Deleers et al.

(10) Patent No.: US 8,802,142 B2
(45) Date of Patent: Aug. 12, 2014

(54) PHARMACEUTICAL COMPOSITIONS COMPRISING LEVETIRACETAM AND PROCESS FOR THEIR PREPARATION

(75) Inventors: Michel Deleers, Linkebeek (BE); Jean-Benoît Hubert, Haaltert (BE)

(73) Assignee: UCB Pharma, S.A., Brussels (BE)

( * ) Notice: Subject to any disclaimer, the term of this patent is extended or adjusted under 35 U.S.C. 154(b) by 1779 days.

(21) Appl. No.: 11/910,167

(22) PCT Filed: Jul. 24, 2006

(86) PCT No.: PCT/EP2006/007260
§ 371 (c)(1),
(2), (4) Date: Jun. 23, 2008

(87) PCT Pub. No.: WO2007/012439
PCT Pub. Date: Feb. 1, 2007

(65) Prior Publication Data
US 2008/0269316 A1    Oct. 30, 2008

(30) Foreign Application Priority Data

Jul. 26, 2005  (EP) ..................................... 05016189
Aug. 4, 2005   (EP) ..................................... 05016945

(51) Int. Cl.
*A61K 9/20*      (2006.01)
*A01N 43/36*     (2006.01)
*A61K 31/40*     (2006.01)
*A61K 9/28*      (2006.01)
*A61K 31/4015*   (2006.01)

(52) U.S. Cl.
CPC .............. *A61K 9/2866* (2013.01); *A61K 9/284* (2013.01); *A61K 31/4015* (2013.01)
USPC .......................................... 424/464; 514/423

(58) Field of Classification Search
USPC .......................................... 424/464; 514/423
See application file for complete search history.

(56) References Cited

U.S. PATENT DOCUMENTS

| 4,837,223 A | 6/1989 | Gobert et al. |
| 4,943,639 A | 7/1990 | Gobert et al. |
| 6,699,502 B1 | 3/2004 | Fanara et al. |
| 2004/0092575 A1 | 5/2004 | Peuvot et al. |
| 2006/0165796 A1 | 7/2006 | Kshirsagar et al. |

FOREIGN PATENT DOCUMENTS

| WO | WO94/09159 | * | 4/1994 |
| WO | 01/39779 A1 | | 6/2001 |
| WO | WO 03/094913 A1 | | 11/2003 |
| WO | 2004/051222 A2 | | 6/2004 |

(Continued)

OTHER PUBLICATIONS

Keppra (2003 Keppra Prescribing Information).*

(Continued)

*Primary Examiner* — Benjamin Packard
(74) *Attorney, Agent, or Firm* — McDonnell Boehnen Hulbert & Berghoff LLP

(57) ABSTRACT

The present invention relates to a pharmaceutical composition comprising levetiracetam as active ingredient and 2.0 to 9.0% per weight of disintegrant, 0.0 to 3.0% per weight of gliding agent, 0.5 to 6.0% per weight of binder, and 0.0 to 1.0% per weight of lubricant, with respect to the total weight of the pharmaceutical composition, and to a process for its preparation.

36 Claims, 6 Drawing Sheets

(56) References Cited

FOREIGN PATENT DOCUMENTS

| WO | 2004/066910 A2 | 8/2004 |
|---|---|---|
| WO | WO 2004/069796 A2 | 8/2004 |
| WO | WO 2004/105682 A2 | 12/2004 |

OTHER PUBLICATIONS

Rote Liste Service GMBH: "Rote Liste 2003" 2002, EVC Editio Cantor, XP-002353197.
Aulton, M.E., "Pharmaceutics—The Science of Dosage Form Design," 2002, XP-002396921.
Rote Liste Service GMBH: "Rote Liste 2003", 2002, EVC Editio Cantor, XP-002353197.
Rote Liste GMBH: "Rote Liste 2006: 2006," ECV Editio Cantor, Aulendorf, Germany.
Rote Liste GMBH: "Rote Liste 2007: 2007," ECV Editio Cantor, Aulendorf, Germany.
Anonymous: "Summary of Product Characteristics Keppra," Sep. 18, 2009, pp. 1-57, Retrieved from the Internet: URL:http://www.ema.europa.eu/hmandocs/pdfs/epar/keppra/emea-combined-h277en.pdf [retrieved on Jul. 8, 2010].
Gower, A.J. et al., "Effects of levetiracetam, a novel antiepileptic drug, on convulsant activity in two genetic rat models of epilepsy", Epilepsy Research, vol. 22, 1995, 207-213.
Noyer, M. et al., "The novel antiepileptic drug levetiracetam (ucb L059) appears to act via a specific binding site in CNS membranes", European Journal of Pharmacology, vol. 286, 1995, 137-146.
Ben-Menachem, E. et al., "Efficacy and Tolerability of Levetiracetam 3000 mg/d in Patients with Refractory Partial Seizures: A Multicenter, Double-Blind, Responder-Selected Study Evaluating Monotherapy", Epilepsy, 41(10), 2000, 1276-1283.
Guay, D. R. P. et al., "Oxcarbazepine, Topiramate, Zonisamide, and Levetiracetam: Potential Use in Neuropathetic Pain", The American Journal of Geriatric Pharmacotherapy, 1(1), 2003, 18-37.
Miller, G. S., MD et al., "Efficacy and Safety of Levetiracetam in Pediatric Migraine", Headache, vol. 44, 2004, 238-243.
Hill, M. P., PhD et al., "Novel Antiepileptic Drug Levetiracetam Decreases Dyskinesia Elicited by L-Dopa and Ropinirole in the MPTP-Lesioned Marmoset", Movement Disorders, 18(11), 2003, 1301-1371.

* cited by examiner

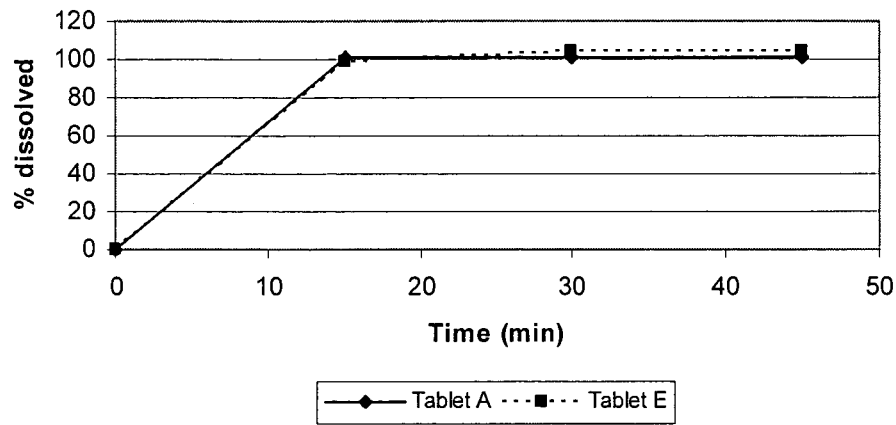
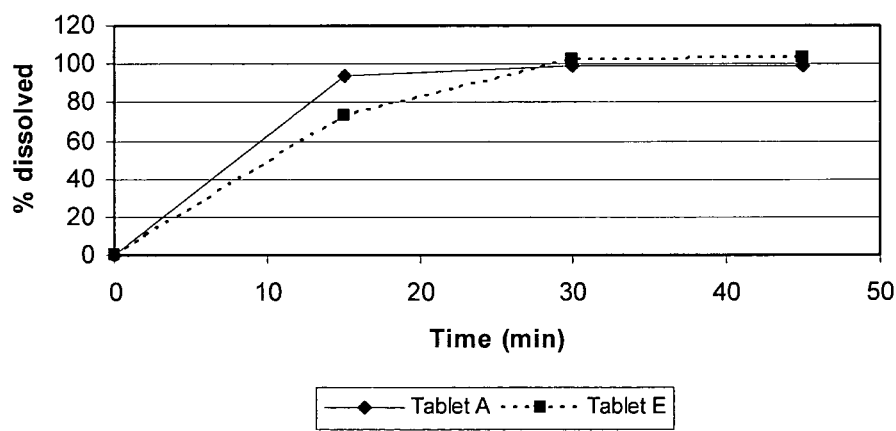

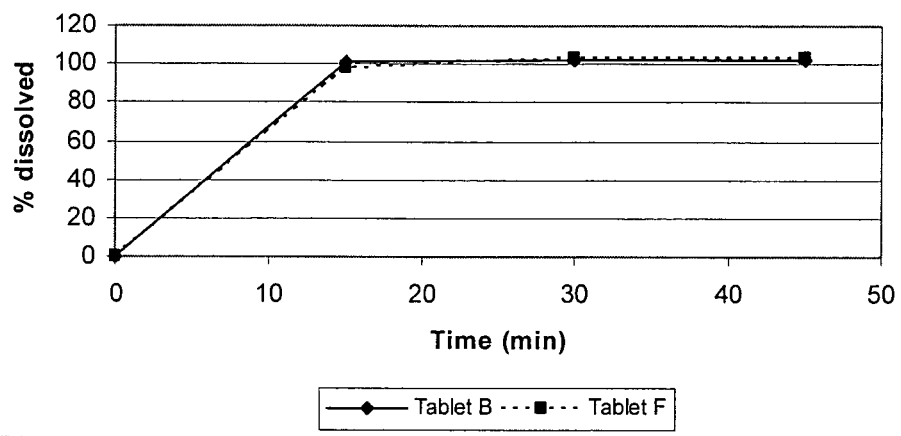
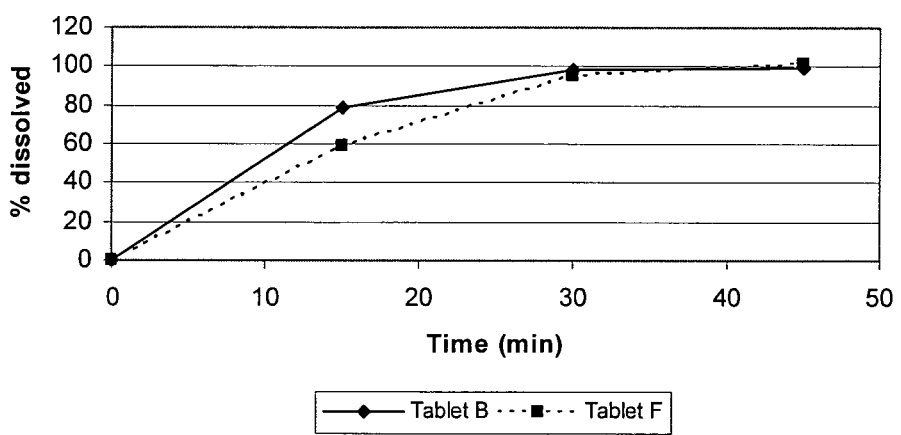

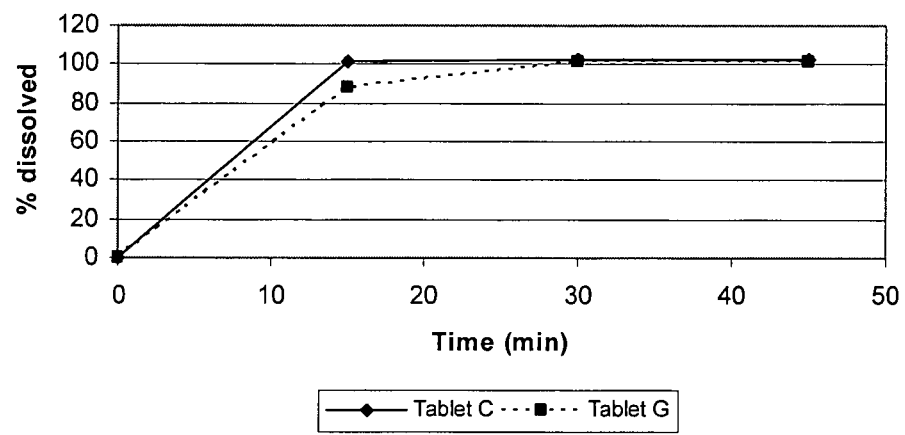
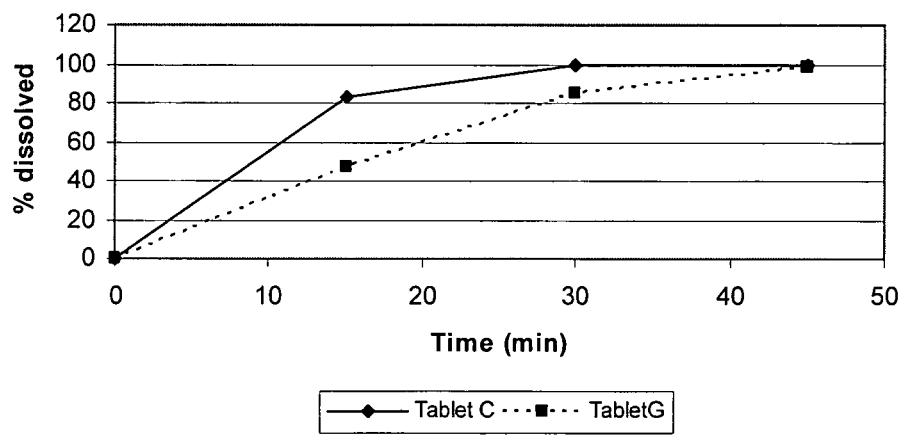

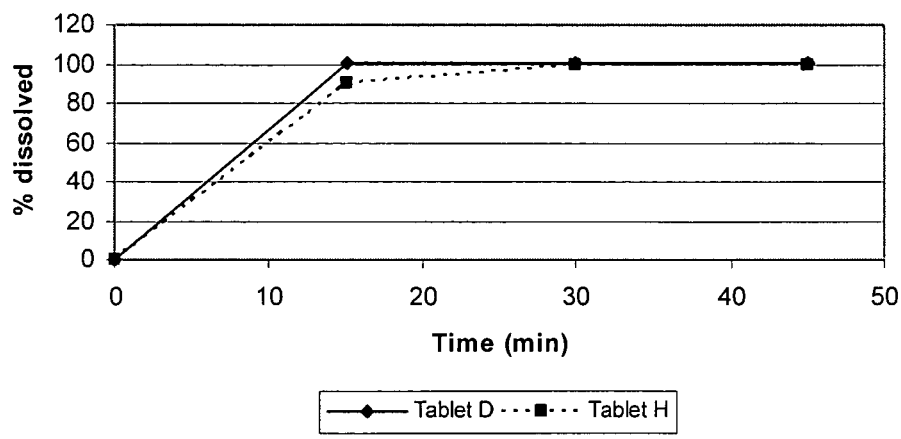
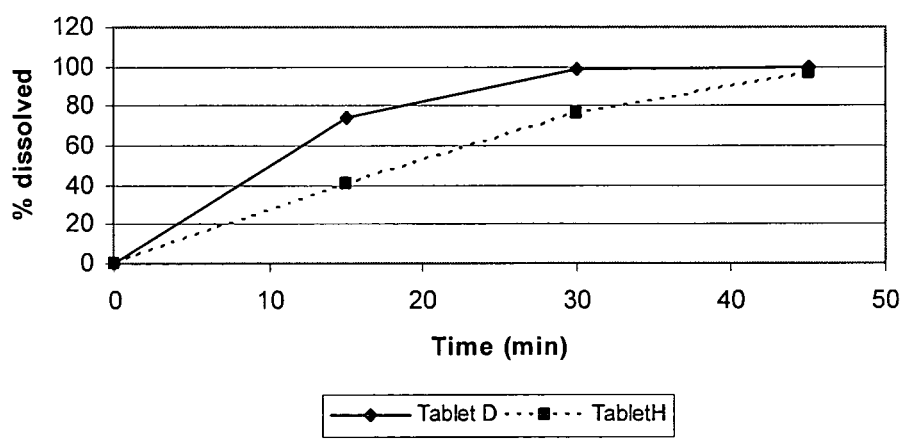

PHARMACEUTICAL COMPOSITIONS COMPRISING LEVETIRACETAM AND PROCESS FOR THEIR PREPARATION

CROSS-REFERENCE TO RELATED APPLICATIONS

This application is a U.S. National Stage of International Application No. PCT/EP2006/007260, filed Jul. 24, 2006.

The present invention relates to a novel pharmaceutical composition comprising levetiracetam and to a process for its preparation.

Levetiracetam or (S)-(−)-α-ethyl-2-oxo-1-pyrrolidine acetamide, a laevorotatory compound, is disclosed as a protective agent for the treatment and the prevention of hypoxic and ischemic type aggressions of the central nervous system in the European patent No. EP 0 162 036 B and has the following formula.

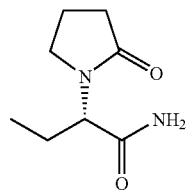

This compound is also effective in the treatment of epilepsy, a therapeutic indication for which it has been demonstrated that its dextrorotatory enantiomer (R)-(−)-α-ethyl-2-oxo-1-pyrrolidine acetamide completely lacks activity (A. J. Gower et al., Eur. J. Pharmacol., 222, 1992, 193-203).

A film-coated tablet containing 250 mg, 500 mg or 1000 mg levetiracetam is described in Rote Liste Service Gmbh "Rote Liste 2003, 2002, ECV—Editio Cantor, Aulendorf, Germany. The ingredients are maize starch, povidone K30, talc, colloidal anhydrous silica, magnesium stearate, and in the coating hypromellose, macrogol 4000, titanium dioxide.

Pharmaceutical compositions comprising levetiracetam may present modified kinetics of release of the active substance as times goes along. This may lead to a slower release in time of the active ingredient and thus to reduced stability of the pharmaceutical composition. One of the consequences of this reduced stability may be an earlier expiry date of the pharmaceutical composition.

According to one aspect, the present invention relates to a pharmaceutical composition comprising levetiracetam as active ingredient and
   2.0 to 9.0% per weight of disintegrant,
   0.0 to 3.0% per weight of gliding agent,
   0.5 to 6.0% per weight of binder, and
   0.0 to 1.0% per weight of lubricant,
with respect to the total weight of the pharmaceutical composition.

The term "active ingredient" as used herein is defined as a substance which has a therapeutic effect.

The amount of the active ingredient present in the pharmaceutical composition of the invention may vary depending on the mammal to which the compositions are administered and the disease to be treated.

The term "disintegrant" as used herein is defined as an accelerating agent of the desintegration of the tablet and the dispersion of the active ingredient in water or gastrointestinal fluids. The disintegrant may be present in the pharmaceutical composition in the form of a single compound or in the form of a mixture of compounds.

Examples of disintegrant are starches, sodium croscarmellose, also referred to as cross-linked sodium carboxymethylcellulose, and polyvinylpolypyrrolidone. Preferred disintegrants according to the present invention are polyvinylpolypyrrolidone, sodium starch glycolate and sodium croscarmellose. More preferred disintegrant according to the present invention is sodium croscarmellose.

Preferably, the pharmaceutical composition according to the present invention comprises 3.0 to 7.0% per weight of disintegrant, more preferably 3.0 to 5.0% per weight of disintegrant, most preferably 3.9% per weight of disintegrant with respect to the total weight of the pharmaceutical composition.

The term "gliding agent" as used herein is defined as an agent improving the fluidity of the powder and thus the filling of the compression chamber of the tablet press. The gliding agent may be present in the pharmaceutical composition in the form of a single compound or in the form of a mixture of compounds.

Examples of gliding agents are talc, starches, stearic acid and anhydrous colloidal silica. Preferred gliding agent according to the present invention is anhydrous colloidal silica.

Preferably, the pharmaceutical composition according to the present invention comprises 0.5 to 2.5% per weight of gliding agent, more preferably 1.0 to 2.0% per weight of gliding agent, most preferably 1.9% per weight of gliding agent with respect to the total weight of the pharmaceutical composition.

The term "binder" as used herein is defined as an agent able to bind particles which cannot be bound only by a compression force. The binder may be present in the form of a single compound or in the form of a mixture of compounds.

Examples of binders are macrogols, microcrystalline cellulose, saccharose, mannitol or sorbitol. Preferred binders according to the present invention are macrogols. Most preferred binder according to the present invention is polyethylene glycol 6000, also referred to as macrogol 6000.

As will be understood by the person skilled in the art, the number "6000" after polyethylene glycol refers to the average molecular weight of the polyethylene glycol.

Usually, the pharmaceutical composition according to the present invention comprises 0.5 to 4.0% per weight of binder with respect to the total weight of the pharmaceutical composition.

Particularly, the pharmaceutical composition according to the present invention comprises 0.5% to 2.5% per weight of binder with respect to the total weight of the pharmaceutical composition.

Preferably, the pharmaceutical composition according to the present invention comprises 0.7 to 1.8% per weight of binder, more preferably 0.8 to 1.6% per weight of binder, most preferably 0.9% of binder with respect to the total weight of the pharmaceutical composition.

The term "lubricant" as used herein is defined as an agent able to decrease adhesion of a powder to punches and friction between particles. The lubricant may be present in the pharmaceutical composition in the form of a single compound or in the form of a mixture of compounds.

Examples of lubricants are talc, magnesium stearate or calcium stearate.

Preferred lubricant according to the present invention is magnesium stearate.

Usually, the pharmaceutical composition according to the present invention comprises 0.0 to 0.75% per weight of lubricant with respect to the total weight of the pharmaceutical composition.

Particularly, the pharmaceutical composition according to the present invention comprises 0.0 to 0.50% per weight of lubricant with respect to the total weight of the pharmaceutical composition.

The pharmaceutical composition according to the present invention comprises preferably 0.05 to 0.25% per weight of lubricant, more preferably 0.08 to 0.15% per weight of lubricant, most preferably 0.11% per weight of lubricant with respect to the total weight of the pharmaceutical composition.

The pharmaceutical composition according to the present invention presents an increased stability in time of the release of levetiracetam as active ingredient compared to known pharmaceutical compositions comprising levetiracetam. Particularly, the pharmaceutical composition according to the present invention presents an increased stability in time of the release of levetiracetam as active ingredient compared to pharmaceutical compositions comprising levetiracetam manufactured by conventional processes, for example wet granulation process.

Preferably, the pharmaceutical composition according to the present invention ensures substantially stable release of the active ingredient as time goes by.

In one embodiment, the pharmaceutical composition according to the present invention comprises at least 2.0 to 9.0% per weight of sodium croscarmellose with respect to total weight of the pharmaceutical composition.

In another embodiment, the pharmaceutical composition according to the present invention comprises at least 0.0 to 3.0% per weight of anhydrous colloidal silica with respect to total weight of the pharmaceutical composition.

In yet another embodiment, the pharmaceutical composition according to the present invention comprises 0.5 to 6.0% per weight of polyethylene glycol 6000 with respect to total weight of the pharmaceutical composition.

In a further embodiment, the pharmaceutical composition according to the present invention comprises 0.0 to 1.0% per weight of magnesium stearate with respect to total weight of the pharmaceutical composition.

Usually, the present invention relates to a pharmaceutical composition comprising levetiracetam as active ingredient and
  2.0 to 9.0% per weight of disintegrant,
  0.0 to 3.0% per weight of gliding agent,
  0.5 to 4.0% per weight of binder, and
  0.0 to 0.75% per weight of lubricant,
with respect to the total weight of the pharmaceutical composition.

Particularly, the present invention relates to a pharmaceutical composition comprising levetiracetam as active ingredient and
  2.0 to 9.0% per weight of disintegrant,
  0.0 to 3.0% per weight of gliding agent,
  0.5 to 2.5% per weight of binder, and
  0.0 to 0.50% per weight of lubricant,
with respect to the total weight of the pharmaceutical composition.

Preferably, the present invention relates to a pharmaceutical composition comprising levetiracetam as active ingredient and
  3.0 to 7.0% per weight of disintegrant,
  0.5 to 2.5% per weight of gliding agent,
  0.7 to 1.8% per weight of binder, and
  0.05 to 0.25% per weight of lubricant,
with respect to the total weight of the pharmaceutical composition.

More preferably, the present invention relates to a pharmaceutical composition comprising levetiracetam as active ingredient and
  3.0 to 5.0% per weight of disintegrant,
  1.0 to 2.0% per weight of gliding agent,
  0.8 to 1.6% per weight of binder, and
  0.08 to 0.15% per weight of lubricant,
with respect to the total weight of the pharmaceutical composition.

Usually, the pharmaceutical composition according to the present invention comprises 80 to 95% per weight of levetiracetam, preferably 85 to 93% per weight of levetiracetam, more preferably 90 to 92% per weight of levetiracetam with respect to the total weight of the pharmaceutical composition.

In a particular embodiment, the present invention relates to a pharmaceutical composition comprising levetiracetam as active ingredient and
  2.0 to 9.0% per weight of sodium croscarmellose,
  0.0 to 3.0% per weight of anhydrous colloidal silica,
  0.5 to 6.0% per weight of polyethylene glycol 6000, and
  0.0 to 1.0% per weight of magnesium stearate,
with respect to the total weight of the pharmaceutical composition.

Usually, in this particular embodiment, the present invention relates to a pharmaceutical composition comprising levetiracetam as active ingredient and
  2.0 to 9.0% per weight of sodium croscarmellose,
  0.0 to 3.0% per weight of anhydrous colloidal silica,
  0.5 to 4.0% per weight of polyethylene glycol 6000, and
  0.0 to 0.75% per weight of magnesium stearate,
with respect to the total weight of the pharmaceutical composition.

Particularly, in this particular embodiment, the present invention relates to a pharmaceutical composition comprising levetiracetam as active ingredient and
  2.0 to 9.0% per weight of sodium croscarmellose,
  0.0 to 3.0% per weight of anhydrous colloidal silica,
  0.5 to 2.5% per weight of polyethylene glycol 6000, and
  0.0 to 0.50% per weight of magnesium stearate,
with respect to the total weight of the pharmaceutical composition Preferably, in this particular embodiment, the present invention relates to a pharmaceutical composition comprising levetiracetam as active ingredient and
  3.0 to 7.0% per weight of sodium croscarmellose,
  0.5 to 2.5% per weight of anhydrous colloidal silica,
  0.7 to 1.8% per weight of polyethylene glycol 6000, and
  0.05 to 0.25% per weight of magnesium stearate
with respect to the total weight of the pharmaceutical composition.

More preferably, in this particular embodiment, the present invention relates to a pharmaceutical composition comprising levetiracetam as active ingredient and
  3.0 to 5.0% per weight of sodium croscarmellose,
  1.0 to 2.0% per weight of anhydrous colloidal silica,
  0.8 to 1.6% per weight of polyethylene glycol 6000, and
  0.08 to 0.15% per weight of magnesium stearate.

In a further particular embodiment, the present invention relates to a pharmaceutical composition comprising
  80 to 95% per weight of levetiracetam,
  2.0 to 9.0% per weight of sodium croscarmellose,
  0.0 to 3.0% per weight of anhydrous colloidal silica,
  0.5 to 6.0% per weight of polyethylene glycol 6000, and
  0.0 to 1.0% per weight of magnesium stearate, with respect to the total weight of the pharmaceutical composition.

Usually, in this further particular embodiment, the present invention relates to a pharmaceutical composition comprising
- 80 to 95% per weight of levetiracetam
- 2.0 to 9.0% per weight of sodium croscarmellose,
- 0.0 to 3.0% per weight of anhydrous colloidal silica,
- 0.5 to 4.0% per weight of polyethylene glycol 6000, and
- 0.0 to 0.75% per weight of magnesium stearate with respect to the total weight of the pharmaceutical composition.

Particularly, in this further particular embodiment, the present invention relates to a pharmaceutical composition comprising
- 80 to 95% per weight of levetiracetam
- 2.0 to 9.0% per weight of sodium croscarmellose,
- 0.0 to 3.0% per weight of anhydrous colloidal silica,
- 0.5 to 2.5% per weight of polyethylene glycol 6000, and
- 0.0 to 0.50% per weight of magnesium stearate with respect to the total weight of the pharmaceutical composition.

Preferably, in this further particular embodiment, the present invention relates to a pharmaceutical composition comprising
- 85 to 93% per weight of levetiracetam
- 3.0 to 7.0% per weight of sodium croscarmellose,
- 0.5 to 2.5% per weight of anhydrous colloidal silica,
- 0.7 to 1.8% per weight of polyethylene glycol 6000, and
- 0.05 to 0.25% per weight of magnesium stearate with respect to the total weight of the pharmaceutical composition.

More preferably, in this further particular embodiment, the present invention relates to a pharmaceutical composition comprising
- 90 to 92% per weight of levetiracetam,
- 3.0 to 5.0% per weight of sodium croscarmellose,
- 1.0 to 2.0% per weight of anhydrous colloidal silica,
- 0.8 to 1.6% per weight of polyethylene glycol 6000, and
- 0.08 to 0.15% per weight of magnesium stearate.

In one embodiment of the present invention, the sum of disintegrant, gliding agent, binder and lubricant present in the pharmaceutical composition comprising levetiracetam as active ingredient is less than or equal to 20% per weight, preferably less than or equal to 15% per weight, more preferably less than or equal to 10% per weight with respect to the total weight of the pharmaceutical composition.

Said values for the sum of disintegrant, gliding agent, binder and lubricant present the further advantage of reducing the size and weight of the pharmaceutical composition for a given quantity of active ingredient thereby increasing the ease of administration to a patient.

Most preferably, the sum of sodium croscarmellose, anhydrous colloidal silica, polyethylene glycol 6000, and magnesium stearate present in the pharmaceutical composition comprising levetiracetam according to the present invention is less than 10% per weight with respect to the total weight of the pharmaceutical composition.

The pharmaceutical composition according to the present invention is preferably administered orally.

The pharmaceutical composition according to the present invention is preferably in the form of a solid, more preferably in the form of a tablet.

The tablet may be uncoated or coated with a coating agent.

In one embodiment, the pharmaceutical composition according to the present invention comprises 1.0 to 6.0% per weight of coating agent, preferably 2.0 to 5.0% per weight of coating agent, more preferably 2.5 to 4.5% per weight of coating agent, most preferably 2.9% per weight of coating agent with respect to the total weight of the pharmaceutical composition.

In a preferred embodiment, the present invention relates to a pharmaceutical composition comprising levetiracetam as active ingredient and
- 2.0 to 9.0% per weight of disintegrant,
- 0 to 3.0% per weight of gliding agent,
- 0.5 to 6.0% per weight of binder,
- 0.0 to 1.0% per weight of lubricant, and
- 1.0 to 6.0% per weight of a coating agent, with respect to the total weight of the pharmaceutical composition.

Usually, in this preferred embodiment, the present invention relates to a pharmaceutical composition comprising levetiracetam as active ingredient and
- 2.0 to 9.0% per weight of disintegrant,
- 0 to 3.0% per weight of gliding agent,
- 0.5 to 4.0% per weight of binder,
- 0.0 to 0.75% per weight of lubricant, and
- 1.0 to 6.0% per weight of a coating agent, with respect to the total weight of the pharmaceutical composition.

Particularly, in this preferred embodiment, the present invention relates to a pharmaceutical composition comprising levetiracetam as active ingredient and
- 2.0 to 9.0% per weight of disintegrant,
- 0 to 3.0% per weight of gliding agent,
- 0.5 to 2.5% per weight of binder,
- 0.0 to 0.50% per weight of lubricant, and
- 1.0 to 6.0% per weight of a coating agent, with respect to the total weight of the pharmaceutical composition.

Preferably, in this preferred embodiment, the present invention relates to a pharmaceutical composition comprising levetiracetam as active ingredient and
- 3.0 to 7.0% per weight of disintegrant,
- 0.5 to 2.5% per weight of gliding agent,
- 0.7 to 1.8% per weight of binder,
- 0.05 to 0.25% per weight of lubricant, and
- 2.0 to 5.0% per weight of coating agent with respect to the total weight of the pharmaceutical composition.

More preferably, in this preferred embodiment, the present invention relates to a pharmaceutical composition comprising levetiracetam as active ingredient and
- 3.0 to 5.0% per weight of disintegrant,
- 1.0 to 2.0% per weight of gliding agent,
- 0.8 to 1.6% per weight of binder,
- 0.08 to 0.15% per weight of lubricant, and
- 2.5 to 4.5% of coating agent, with respect to the total weight of the pharmaceutical composition.

Examples of coating agents are ethylcellulose, hydroxypropylmethylcellulose and methacrylic acid-alkyl acrylate copolymers.

Preferred coating agents are hydroxypropylmethylcellulose aqueous dispersions.

More preferred coating agent according to the present invention is Opadry®.

Opadry® is a hydroxypropylmethylcellulose aqueous dispersion. Examples of Opadry® are Opadry® 85F20694, Opadry® 85F32004, Opadry® 85F23452 and Opadry® 85F18422.

The coating agent preferably comprises polyvinyl alcohol (PVA) which coating agent ensures a better gliding of the tablets upon packaging. More preferably, the coating agent comprises partially hydrolyzed polyvinyl alcohol.

The presence of polyvinyl alcohol in the coating agent may also ensure a better adhesion of the coating to the tablet. Moreover, higher concentrations of coating agents may be used.

In another embodiment, the pharmaceutical composition according to the present invention comprises 1.0 to 6.0% per weight of coating agent comprising polyvinyl alcohol, preferably 2.0 to 5.0% per weight of coating agent comprising polyvinyl alcohol, more preferably 2.5 to 4.5% per weight of coating agent comprising polyvinyl alcohol, most preferably 2.9% per weight of coating agent comprising polyvinyl alcohol with respect to the total weight of the pharmaceutical composition.

In this embodiment, the polyvinyl alcohol is preferably partially hydrolyzed.

In a particular embodiment according to the present invention, the sum of disintegrant, gliding agent, binder, lubricant and coating agent present in the pharmaceutical composition comprising levetiracetam as active ingredient is less than or equal to 20% per weight, preferably less than or equal to 15% per weight, more preferably less than or equal to 10% per weight with respect to the total weight of the pharmaceutical composition.

In a more preferred embodiment, the present invention relates to a pharmaceutical composition comprising levetiracetam as active ingredient and
- 2.0 to 9.0% per weight of sodium croscarmellose,
- 0.0 to 3.0% per weight of anhydrous colloidal silica,
- 0.5 to 6.0% per weight of polyethylene glycol 6000, and
- 0.0 to 1.0% per weight of magnesium stearate,
- 1.0 to 6.0% per weight of Opadry®,
with respect to the total weight of the pharmaceutical composition.

Usually, in this more preferred embodiment, the present invention relates to a pharmaceutical composition comprising levetiracetam as active ingredient and
- 2.0 to 9.0% per weight of sodium croscarmellose,
- 0.0 to 3.0% per weight of anhydrous colloidal silica,
- 0.5 to 4.0% per weight of polyethylene glycol 6000, and
- 0.0 to 0.75% per weight of magnesium stearate,
- 1.0 to 6.0% per weight of Opadry®,
with respect to the total weight of the pharmaceutical composition.

Particularly, in this more preferred embodiment, the present invention relates to a pharmaceutical composition comprising levetiracetam as active ingredient and
- 2.0 to 9.0% per weight of sodium croscarmellose,
- 0.0 to 3.0% per weight of anhydrous colloidal silica,
- 0.5 to 2.5% per weight of polyethylene glycol 6000, and
- 0.0 to 0.50% per weight of magnesium stearate,
- 1.0% to 6.0% per weight of Opadry®,
with respect to the total weight of the pharmaceutical composition.

Preferably, in this more preferred embodiment, the present invention relates to a pharmaceutical composition comprising levetiracetam as active ingredient and
- 3.0 to 7.0% per weight of sodium croscarmellose,
- 0.5 to 2.5% per weight of anhydrous colloidal silica,
- 0.7 to 1.8% per weight of polyethylene glycol 6000,
- 0.05 to 0.25% per weight of magnesium stearate, and
- 2.0 to 5.0% per weight of Opadry®,
with respect to the total weight of the pharmaceutical composition.

More preferably, in this more preferred embodiment, the present invention relates to a pharmaceutical composition comprising levetiracetam as active ingredient and
- 3.0 to 5.0% per weight of sodium croscarmellose,
- 1.0 to 2.0% per weight of anhydrous colloidal silica,
- 0.8 to 1.6% per weight of polyethylene glycol 6000,
- 0.08 to 0.15% per weight of magnesium stearate, and
- 2.5 to 4.5% per weight of Opadry®,
with respect to the total weight of the pharmaceutical composition.

In the above mentioned pharmaceutical compositions, Opadry® preferably comprises polyvinyl alcohol. More preferably, Opadry® comprises partially hydrolyzed polyvinyl alcohol.

In another particular embodiment, the sum of sodium croscarmellose, anhydrous colloidal silica, polyethylene glycol 6000, magnesium stearate and Opadry® in the pharmaceutical composition comprising levetiracetam is less than 10% per weight with respect to the total weight of the pharmaceutical composition.

Optionally, the pharmaceutical composition according to the present invention may contain a diluent or filler.

The term "diluent" or "filler" as used herein is defined as an inert agent designed to increase the weight and/or the size of the pharmaceutical composition, for example in the case of a tablet.

The diluent or the filler may be present in the pharmaceutical composition in the form of a single compound or in the form of a mixture of compounds.

Preferably the diluent of the filler is added when the amount of the active ingredient and the other excipients is too small to obtain a tablet of suitable size.

Examples of diluents or fillers according to the present invention are starches, lactose, mannitol, sugars or mineral salts.

Percentages per weight of diluent or filler necessary to obtain a pharmaceutical composition according to the present invention will be determined according to conventional methods known to the person skilled in the art.

Optionally, the pharmaceutical composition according to the present invention may contain a sweetening agent such as sucrose or saccharine, a coloring agent or a flavoring agent.

Optionally, the pharmaceutical composition according to the present invention may comprise a taste-masking agent.

Preferably, the pharmaceutical composition according to the present invention comprises a coating agent which has taste-masking properties.

Generally, existing pharmaceutical composition comprising levetiracetam are manufactured by a wet granulation process according to conventional methods known to the man skilled in the art.

Such a wet granulation process may cause degradation of the active ingredient upon contact with the liquid phase. Furthermore, such a process requires a drying step which is time consuming and, due to the presence of a heat source, increases costs of production.

Therefore, in another aspect, the present invention relates to a process of manufacturing a pharmaceutical composition comprising levetiracetam as active ingredient and
- 2.0 to 9.0% per weight of disintegrant,
- 0 to 3.0% per weight of gliding agent,
- 0.5 to 6.0% per weight of binder, and
- 0.0 to 1.0% per weight of lubricant,
with respect to the total weight of the pharmaceutical composition, which process comprises the steps of:
i) mixing levetiracetam, the gliding agent, the disintegrant and the binder,
ii) adding the lubricant,
iii) mixing levetiracetam, the gliding agent, the disintegrant, the binder and the lubricant;
iv) compacting the mixture obtained in step iii),
v) grinding the mixture obtained in step iv), and
vi) compressing the mixture obtained in step v).

The term "compacting" as used herein is defined as the transformation of a powder into a coherent specimen of a defined shape by compression (eg by a roller compacter).

The term "grinding" as used herein is defined as the reduction of the particle size by sieving.

The term "compressing" as used herein is defined as the application of a sufficient force by the punches of a tablet press on a powder to compact it into a tablet.

Preferably, at least one of levetiracetam, disintegrant, gliding agent or binder undergoes desagglomeration prior to mixing.

The term "desagglomeration" as used herein is defined as the disruption of agglomerates in the powder.

Preferably, the grinding step is achieved on a sieve of less than 5 mm, more preferably less than 3 mm, most preferably on a sieve of 1.5 mm.

The process according to the present invention comprises fewer steps than the wet granulation process thus ensuring lower costs of production. Furthermore, said process avoids degradation of the active ingredient upon contact with a liquid phase.

Preferably, the process comprises a further coating step in which water, preferably purified water, is added to the coating agent and resulting suspension is sprayed on the mixture resulting from step vi).

Preferred coating agent is Opadry®. More preferred coating agent is selected from Opadry® 85F20694, Opadry® (85F32004, Opadry® 85F23452 and Opadry® 85F18422. Most preferred coating agent comprises polyvinyl alcohol.

The present invention further relates to a process of manufacturing pharmaceutical compositions comprising preferred, more preferred and most preferred percentages per weight of levetiracetam, disintegrant, gliding agent, binder, lubricant and coating agent as defined above for these pharmaceutical compositions, which process comprises steps i) to vi) as defined here above.

In a preferred embodiment, the present invention relates to a process of manufacturing a pharmaceutical composition comprising levetiracteam as active ingredient and
2.0 to 9.0% per weight of sodium croscarmellose,
0.0 to 3.0% per weight of anhydrous colloidal silica,
0.5 to 6.0% per weight of polyethylene glycol 6000, and
0.0 to 1.0% per weight of magnesium stearate,
with respect to the total weight of the pharmaceutical composition,
which process comprises the steps of:
i) mixing levetiracetam, anhydrous collidal silica, sodium croscarmellose, polyethylene glycol 6000,
ii) adding magnesium stearate,
iii) mixing levetiracetam, anhydrous collidal silica, sodium croscarmellose, polyethylene glycol 6000 and magnesium stearate;
iv) compacting mixture obtained in step iii),
v) grinding mixture obtained in step iv), and
vi) compressing mixture obtained in step v).

In a more preferred embodiment, the present invention relates to a process of manufacturing a pharmaceutical composition comprising levetiracetam as active ingredient and
2.0 to 9.0% per weight of sodium croscarmellose,
0.0 to 3.0% per weight of anhydrous colloidal silica,
0.5 to 6.0% per weight of polyethylene glycol 6000,
0.0 to 1.0% per weight of magnesium stearate,
1.0 to 6.0% per weight of Opadry®
with respect to the total weight of the pharmaceutical composition,
which process comprises the steps of:
i) mixing levetiracetam, anhydrous collidal silica, sodium croscarmellose, polyethylene glycol 6000,
ii) adding magnesium stearate,
iii) mixing levetiracetam, anhydrous collidal silica, sodium croscarmellose, polyethylene glycol 6000 and magnesium stearate;
iv) compacting mixture obtained in step iii),
v) grinding mixture obtained in step iv),
vi) compressing mixture obtained in step v), and
vii) spraying onto the mixture obtained in step vi) a suspension of hydroxypropylmethylcellulose comprising Opadry®.

In this more preferred embodiment, Opadry® preferably comprises polyvinyl alcohol.

The present invention further relates to a process of manufacturing pharmaceutical compositions comprising usual, particular, preferred, more preferred and most preferred percentages per weight of levetiracetam, sodium croscarmellose, anhydrous colloidal silica, polyethylene glycol 6000, magnesium stearate and Opadry® as defined above for these pharmaceutical compositions, which process comprises steps i) to vii) as defined here above.

In another aspect the present invention relates to a pharmaceutical composition comprising levetiracetam and
2.0 to 9.0% per weight of disintegrant,
0 to 3.0% per weight of gliding agent,
0.5 to 6.0% per weight of binder, and
0.0 to 1.0% per weight of lubricant,
with respect to the total weight of the pharmaceutical composition,
useful for the treatment or prevention of a disease.

By the term "disease", we understand a disease selected from the group consisting of epileptogenesis, seizure disorders, convulsions, Parkinson's disease, dyskinesia induced by dopamine replacement therapy, tardive dyskinesia induced by administration of neuroleptic drugs, Huntington Chorea, and other neurological disorders including bipolar disorders, mania, depression, anxiety, attention deficit hyperactivity disorder (ADHD), migraine, trigeminal and other neuralgia, chronic pain, neuropathic pain, cerebral ischemia, cardiac arrhythmia, myotonia, cocaine abuse, stroke, myoclonus, tremor, essential tremor, simple or complex tics, Tourette syndrome, restless leg syndrome and other movement disorders, neonatal cerebral haemorrhage, amyotrophic lateral sclerosis, spasticity and degenerative diseases, bronchial asthma, asthmatic status and allergic bronchitis, asthmatic syndrome, bronchial hyperreactivity and bronchospastic syndromes as well as allergic and vasomotor rhinitis and rhinoconjunctivitis.

The term "treatment" as used herein, includes curative treatment and prophylactic treatment.

By "curative" is meant efficacy in treating a current symptomatic episode of a disorder or condition.

By "prophylactic" is meant prevention of the occurrence or recurrence of a disorder or condition.

The present invention concerns also a method for treatment of a human patient by using the pharmaceutical composition.

The present invention concerns also the pharmaceutical composition for use as a medicament for curing the said disease.

The present invention concerns also the use of the pharmaceutical composition for the manufacture of a medicament for a therapeutic application in the said disease.

Preferably said disease is selected from the group consisting essentially of epilepsy, Parkinson's disease, dyskinesia, migraine, tremor, essential tremor, bipolar disorders, chronic pain, neuropathic pain, or bronchial, asthmatic or allergic conditions. More preferably said disease is epilepsy.

The present invention concerns also a method for manufacturing a medicament intended for therapeutic application in the said disease, characterized in that the pharmaceutical composition according to the present invention is used.

The present invention is also directed to methods of treating humans to alleviate disease by the administration of the pharmaceutical composition.

FIG. 3 shows comparative dissolution kinetics for pharmaceutical composition A of example 1 according to our invention and known pharmaceutical composition E of example 2 immediately after manufacturing.

FIG. 4 shows comparative dissolution kinetics for pharmaceutical composition A of example 1 according to our invention and known pharmaceutical composition E of example 2 six months after manufacturing.

FIG. 5 shows comparative dissolution kinetics for pharmaceutical composition B of example 1 according to our invention and known pharmaceutical composition F of example 2 immediately after manufacturing.

FIG. 6 shows comparative dissolution kinetics for pharmaceutical composition B of example 1 according to our invention and known pharmaceutical composition F of example 2 six months after manufacturing.

FIG. 7 shows comparative dissolution kinetics for pharmaceutical composition C of example 1 according to our invention and known pharmaceutical composition G of example 2 immediately after manufacturing.

FIG. 8 shows comparative dissolution kinetics for pharmaceutical composition C of example 1 according to our invention and known pharmaceutical composition G of example 2 six months after manufacturing.

FIG. 9 shows comparative dissolution kinetics for pharmaceutical composition D of example 1 according to our invention and known pharmaceutical composition H of example 2 immediately after manufacturing.

FIG. 10 shows comparative dissolution kinetics for pharmaceutical composition D of example 1 according to our invention and known pharmaceutical composition H of example 2 six months after manufacturing.

The following examples are provided for illustrative purposes only and are not intended, nor should they be construed, as limiting the invention in any manner. Those skilled in the art will appreciate that routine variations and modifications of the following examples can be made without exceeding the spirit or scope of the invention.

EXAMPLES

Example 1

Figure 1:
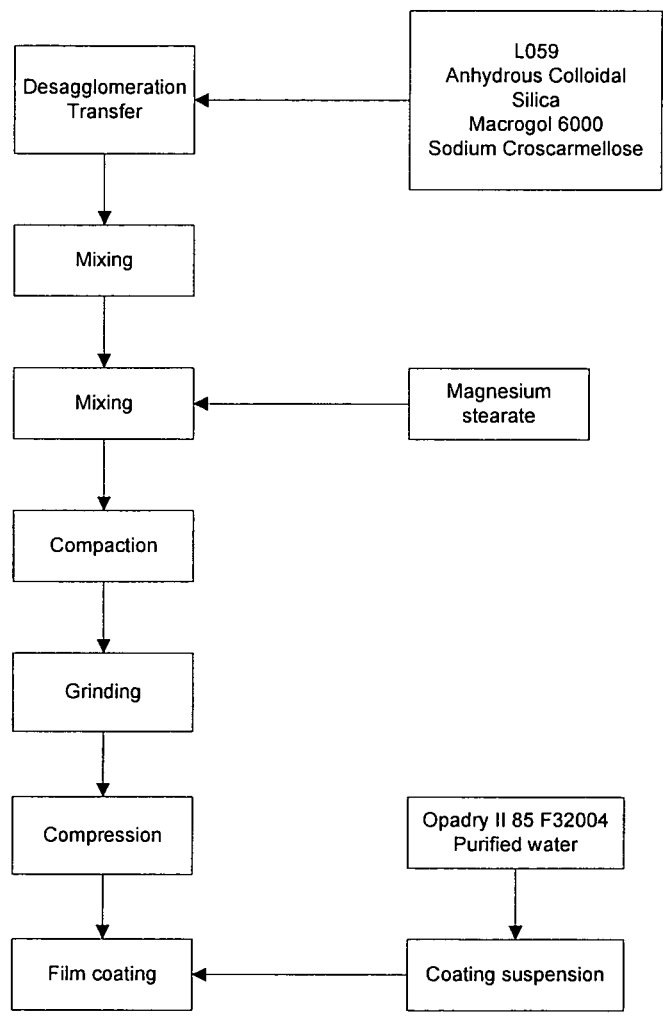
FIG. 1 shows a flow chart of the process according to the present invention.

Table I shows four pharmaceutical compositions (A, B, C and D) with different quantities of active ingredient levetiracetam which were manufactured according to the process disclosed in FIG. 1, referred to as dry granulation process.

TABLE I

| Components | Composition | | | |
| --- | --- | --- | --- | --- |
| | A Quantities in mg | B Quantities in mg | C Quantities in mg | D Quantities in mg |
| Levetiracetam | 250 | 500 | 750 | 1000 |
| Sodium croscarmellose | 10.75 | 21.50 | 32.25 | 43.00 |
| Macrogol 6000 | 2.50 | 5.00 | 7.50 | 10.00 |
| Anhydrous colloidal silica | 5.188 | 10.375 | 15.563 | 20.75 |
| Magnesium stearate | 0.313 | 0.625 | 0.938 | 1.25 |
| Opadry ® comprising polyvinyl alcohol | 8.063 | 16.125 | 24.188 | 32.25 |

Example 2

Figure 2:
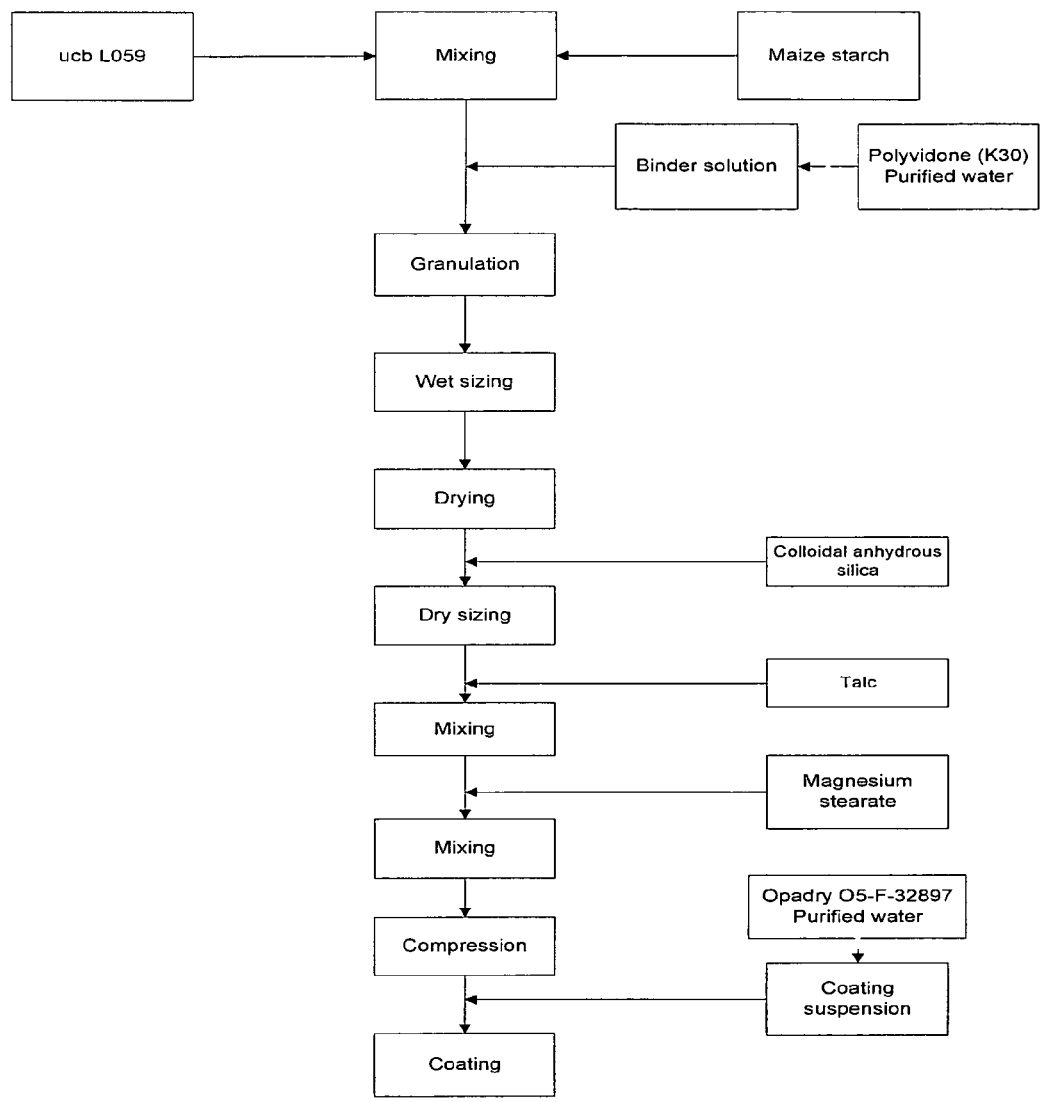
FIG. 2 shows a flow chart of the wet granulation process.

Table II shows four pharmaceutical compositions (E, F, G and H) with different quantities of active ingredient levetiracetam which were manufactured according to the process disclosed in FIG. 2, referred to as wet granulation process. These compositions are not within the scope of the present invention and have been manufactured for comparative study.

TABLE II

| Components | Composition | | | |
| --- | --- | --- | --- | --- |
| | E Quantities in mg | F Quantities in mg | G Quantities in mg | H Quantities in mg |
| Levetiracetam | 250.00 | 500.00 | 750.00 | 1000.0 |
| Corn starch | 58.00 | 116.00 | 174.00 | 232.00 |

TABLE II-continued

| | Composition | | | |
|---|---|---|---|---|
| Components | E Quantities in mg | F Quantities in mg | G Quantities in mg | H Quantities in mg |
| Polyvinyl pyrrolidone | 7.50 | 15.00 | 22.50 | 30.00 |
| Anhydrous colloidal silica | 4.00 | 8.00 | 12.00 | 16.00 |
| Talc | 5.00 | 10.00 | 15.00 | 20.00 |
| Magnesium stearate | 0.50 | 1.00 | 1.50 | 2.00 |
| Opadry ® | 10.00 | 20.00 | 30.00 | 40.00 |

Example 3

Kinetics of release of active ingredient have been measured for compositions A to H. These kinetics have been measured for all compositions immediately after manufacturing and six months after manufacturing. During these six months, the pharmaceutical compositions have been kept under blister at 40° C. and at a level of relative humidity of 75%.

The dissolution tests are made in an USP Apparatus 2 (paddle apparatus), volume 900 mL, speed 50 rpm, and temperature 37° C.

FIGS. 3 to 10 show that for pharmaceutical compositions manufactured according to the dry granulation process, percentages of dissolution are more stable than for compositions manufactured according to the wet granulation process. This suggests that pharmaceutical compositions A to D are more stable in time than pharmaceutical compositions E to H.

Example 4

The six following pharmaceutical compositions were manufactured according to the process disclosed in FIG. 1, referred to as dry granulation process.

Composition I comprises 1000 mg of levetiracetam, 40 mg of polyvinylpolypyrrolidone, 60 mg of sorbitol and 5 mg of magnesium stearate.

Composition J comprises 1000 mg of levetiracetam, 30 mg of sodium carboxymethylcellulose, 30 mg of starch, 30 mg of macrogol and 1 mg of magnesium stearate.

Composition K comprises 1000 mg of levetiracetam, 40 mg of sodium croscarmellose, 60 mg of microcrystalline cellulose, 5 mg of colloidal silica and 5 mg of calcium stearate.

Composition L comprises 1000 mg of levetiracetam, 40 mg of polyvinylpolypyrrolidone, 10 mg of colloidal silica, 15 mg of talc and 20 mg of macrogol.

Composition M comprises 1000 mg of levetiracetam, 37.5 mg of sodium starch glycolate, 10 mg of colloidal silica, 20 mg of macrogol and 1.25 mg of magnesium stearate.

Composition N comprises 1000 mg of levetiracetam, 30 mg of polyvinylpolypyrrolidone, 20 mg of colloidal silica, 60 mg of mannitol and 5 mg of magnesium stearate.

These compositions were coated with hydroxypropylmethylcellulose aqueous dispersions or polyvinyl alcohol aqueous dispersions.

These 6 compositions are stable.

The invention claimed is:

1. A pharmaceutical composition comprising levetiracetam as active ingredient and
   2.0 to 9.0% per weight of a disintegrant selected from polyvinylpolypyrrolidone and sodium croscarmellose,
   0.0 to 3.0% per weight of gliding agent,
   0.5 to 6.0% per weight of binder selected from macrogol, microcrystalline cellulose, saccharose, mannitol, and sorbitol, and
   0.0 to 1.0% per weight of lubricant,
with respect to the total weight of the pharmaceutical composition.

2. The pharmaceutical composition according to claim 1 comprising 3.0 to 7.0% per weight of disintegrant with respect to the total weight of the pharmaceutical composition.

3. The pharmaceutical composition according to claim 1 comprising 0.5 to 2.5% per weight of gliding agent with respect to the total weight of the pharmaceutical composition.

4. The pharmaceutical composition according to claim 1 comprising 0.5 to 4.0% per weight of binder with respect to the total weight of the pharmaceutical composition.

5. The pharmaceutical composition according to claim 1 comprising 0.8 to 1.6% per weight of binder with respect to the total weight of the pharmaceutical composition.

6. The pharmaceutical composition according to claim 1 comprising 0.0 to 0.75% per weight of lubricant with respect to the total weight of the pharmaceutical composition.

7. The pharmaceutical composition according to claim 1 comprising 0.0 to 0.50% per weight of lubricant with respect to the total weight of the pharmaceutical composition.

8. The pharmaceutical composition according to claim 1 comprising 0.08 to 0.15% per weight of lubricant with respect to the total weight of the pharmaceutical composition.

9. The pharmaceutical composition according to claim 1 wherein the sum of disintegrant, gliding agent, binder and lubricant is less than or equal to 20% per weight with respect to the total weight of the pharmaceutical composition.

10. The pharmaceutical composition according to claim 1 wherein the disintegrant is sodium croscarmellose.

11. The pharmaceutical composition according to claim 1 wherein the gliding agent is anhydrous colloidal silica.

12. The pharmaceutical composition according to claim 1 wherein the binder is polyethylene glycol 6000.

13. The pharmaceutical composition according to claim 1 wherein the lubricant is magnesium stearate.

14. The pharmaceutical composition according to claim 1 comprising 2.0 to 9.0% per weight of sodium croscarmellose with respect to total weight of the pharmaceutical composition.

15. The pharmaceutical composition according to claim 1 comprising 0.0 to 3.0% per weight of anhydrous colloidal silica with respect to total weight of the pharmaceutical composition.

16. The pharmaceutical composition according to claim 1 comprising 0.5 to 6.0% per weight of polyethylene glycol 6000 with respect to total weight of the pharmaceutical composition.

17. The pharmaceutical composition according to claim 1 comprising 0.0 to 1.0% per weight of magnesium stearate with respect to total weight of the pharmaceutical composition.

18. The pharmaceutical composition according to claim 1 which comprises 80% to 95% per weight of levetiracetam.

19. The pharmaceutical composition according to claim 1 which comprises a coating agent.

20. The pharmaceutical composition according to claim 19 wherein the coating agent comprises polyvinyl alcohol.

21. The pharmaceutical composition according to claims 19 wherein the coating agent is hydroxypropylmethylcellulose aqueous dispersions.

22. The pharmaceutical composition according to claim 1 which is a tablet.

23. A process of manufacturing a pharmaceutical composition comprising levetiracetam as active ingredient and
  2.0 to 9.0% per weight of a disintegrant selected from polyvinylpolypyrrolidone and sodium croscarmellose,
  0 to 3.0% per weight of gliding agent,
  0.5 to 6.0% per weight of a binder selected from macrogol, microcrystalline cellulose, saccharose, mannitol, and sorbitol, and
  0.0 to 1.0% per weight of lubricant,
with respect to the total weight of the pharmaceutical composition,
which process comprises:
i) mixing levetiracetam, the gliding agent, the disintegrant and the binder,
ii) adding the lubricant,
iii) mixing levetiracetam, the gliding agent, the disintegrant, the binder and the lubricant;
iv) compacting the mixture obtained in iii),
v) grinding the mixture obtained in iv), and
vi) compressing the mixture obtained in v).

24. The pharmaceutical composition according to claim 1 comprising 250 mg of levetiracetam, 10.75 mg of sodium croscarmellose, 5.188 mg of anhydrous colloidal silica, 2.50 mg of polyethylene glycol 6000, and 0.313 of magnesium stearate.

25. The pharmaceutical composition according to claim 1 comprising 500 mg of levetiracetam, 21.50 mg of sodium croscarmellose, 10.375 mg of anhydrous colloidal silica, 5.00 mg of polyethylene glycol 6000, and 0.625 of magnesium stearate.

26. A pharmaceutical composition made according to the process of claim 23.

27. The pharmaceutical composition according to claim 26 wherein the disintegrant is sodium croscarmellose.

28. The pharmaceutical composition according to claim 26 wherein the gliding agent is anhydrous colloidal silica.

29. The pharmaceutical composition according to claim 26 wherein the lubricant is magnesium stearate.

30. The pharmaceutical composition according to claim 27 comprising 2.0 to 9.0% per weight of sodium croscarmellose with respect to total weight of the pharmaceutical composition.

31. The pharmaceutical composition according to claim 28 comprising 0.0 to 3.0% per weight of anhydrous colloidal silica with respect to total weight of the pharmaceutical composition.

32. The pharmaceutical composition according to claim 29 comprising 0.0 to 1.0% per weight of magnesium stearate with respect to total weight of the pharmaceutical composition.

33. The pharmaceutical composition according to claim 26 comprising 250 mg of levetiracetam, 10.75 mg of sodium croscarmellose, 5.188 mg of anhydrous colloidal silica, 2.50 mg of polyethylene glycol 6000, and 0.313 of magnesium stearate.

34. The pharmaceutical composition according to claim 26 comprising 500 mg of levetiracetam, 21.50 mg of sodium croscarmellose, 10.375 mg of anhydrous colloidal silica, 5.00 mg of polyethylene glycol 6000, and 0.625 of magnesium stearate.

35. The pharmaceutical composition according to claim 1 comprising 750 mg of levetiracetam, 32.25 mg of sodium croscarmellose, 15.563 mg of anhydrous colloidal silica, 7.50 mg of polyethylene glycol 6000, and 24.188 of magnesium stearate.

36. The pharmaceutical composition according to claim 1 comprising 1000 mg of levetiracetam, 43.00 mg of sodium croscarmellose, 20.75 mg of anhydrous colloidal silica, 10.00 mg of polyethylene glycol 6000, and 32.25 of magnesium stearate.

* * * * *

UNITED STATES PATENT AND TRADEMARK OFFICE
CERTIFICATE OF CORRECTION

| | | |
|---|---|---|
| PATENT NO. | : 8,802,142 B2 | Page 1 of 1 |
| APPLICATION NO. | : 11/910167 | |
| DATED | : August 12, 2014 | |
| INVENTOR(S) | : Deleers et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1838 days.

Signed and Sealed this
Fourth Day of August, 2015

Michelle K. Lee
*Director of the United States Patent and Trademark Office*